United States Patent [19]

Wilson

[11] Patent Number: 5,524,622
[45] Date of Patent: Jun. 11, 1996

[54] NON-INVASIVE METHOD OF DETERMINING INFLAMMATION OF THE GASTROINTESTINAL TRACT

[75] Inventor: Richard A. Wilson, Lake Oswego, Oreg.

[73] Assignee: Oregon Health Sciences University, Portland, Oreg.

[21] Appl. No.: 309,255

[22] Filed: Sep. 20, 1994

[51] Int. Cl.$^6$ ..................................................... A61B 6/00
[52] U.S. Cl. ............................ 128/654; 128/659; 378/62; 424/1.11; 424/1.61
[58] Field of Search ................................ 128/653.4, 659, 128/654; 378/62; 424/9

[56] References Cited

U.S. PATENT DOCUMENTS

| | | | |
|---|---|---|---|
| 4,243,652 | 1/1981 | Francis | 128/654 |
| 4,401,647 | 8/1983 | Krohn et al. | 128/659 |
| 4,926,869 | 5/1990 | Rubin et al. | 128/653.4 |
| 5,070,877 | 12/1991 | Mohiuddin et al. | 128/654 |
| 5,287,273 | 2/1994 | Kupfer et al. | 128/653.4 |

FOREIGN PATENT DOCUMENTS 2066664  12/1979  United Kingdom.

OTHER PUBLICATIONS

Blumhagen, J. D., et al., "Gastroesophageal Reflux in Children: Radionuclide Gastroesophagography," *AJR* 135:1001–1004 (Nov. 1980).

Bonow, R., et al., "Identification of Viable Myocardium in Patients With Chronic Coronary Artery Disease and Left Ventricular Dysfunction," *Clinical Invest.* 83:26–37 (Jan. 1991).

Cho, C. H., and Ogle, C. W., "Modulatory Action of Adenosine on Gastric Function and Ethanol-Induced Mucosal Damage in Rats," *Digestive Diseases and Sciences* 35:1334–1339 (Nov. 1990).

Datz, F., "Editorial: Radionuclide Imaging of Joint Inflammation in the '90s," *The Journal of Nuclear Medicine* 31:684–687 (May 1990).

Eikman, E., et al., "Gallium-67 Accumulation in the Stomach in Patients with Postoperative Gastritis," *The Journal of Nuclear Medicine* 21:706–707 (1980).

Fung, W., et al., "Gastroesophageal Scintigraphy and Endoscopy in the Diagnosis of Esophageal Reflux and Esophagitis," *The American Journal of Gastroenterology* 80:245–247 (1985).

Gould, K., et al., "Noninvasive Assessment of Coronary Stenoses by Myocardial Imaging During Pharmacologic Coronary Vasodilatation," *The American Journal of Cardiology* 41:279–287 (Feb. 1978).

(List continued on next page.)

*Primary Examiner*—Krista M. Zele
*Assistant Examiner*—Brian L. Casler
*Attorney, Agent, or Firm*—Klarquist Sparkman Campbell Leigh & Whinston

[57] ABSTRACT

A non-invasive method of determining the presence of inflammation in a region of the gastrointestinal tract of an organism comprises introducing an arterial dilating agent into the circulatory system that provides blood flow to that region, then introducing a blood flow marking medium into the circulation providing blood flow to that region. The amount of blood flow marking medium present in that region is then monitored as an indication of the extent of inflammation present in that region. The capability of inflamed gastrointestinal tract tissue to take up increased amounts of the blood flow marking medium provides an indication of the presence of an abnormal pathologic process in that region of the gastrointestinal tract. In the preferred embodiment of the method, the arterial dilator is dipyridamole. The blood flow marking medium is thallium-201, and its accumulation in the region of the gastrointestinal tract is monitored by measuring the radioactive emissions by thallium-201 scintigraphy. The method permits the non-invasive determination of the presence of inflammation in the gastrointestinal tract of an organism.

10 Claims, 1 Drawing Sheet

OTHER PUBLICATIONS

Hardoff, R., et al., "Gastric Visualization by Ga-67 Scintigraphy and Coarse Gastric Mucosa in a Patient with Hodgkin's Disease," *Interesting Images* 16:124–125 (Jan. 8, 1990).

Jenkins, A. F., et al., "Gatroesophageal Scintigraphy: Is It A Sensitive Screening Test for Gastroesophageal Reflux Disease?," *J. of Clin. Gastro.* 7:127–131 (1985).

Knight, L., et al., "Selenium-75-Labeled Sucralfate: Comparison With Other Radiolabels and Initial Clinical Studies," *Am. J. of Physio. Imaging* 3:10–18 (1988).

Leppo, J., et al., "Serial Thallium-201 Myocardial Imaging After Dipyridamole Infusion: Diagnostic Utility in Detecting Coronary Stenoses and Relationship to Regional Wall Motion," *Circulation* 66:649–657 (Sep. 1982).

MacMahon, H., et al., "Gallium Accumulation in the Stomach A Frequent Incidental Finding," *Clin. Nucl. Med.* 10:719–723 (Oct. 1985).

Miller, J., and Thomas, D., "Uptake of Ga-67 in a Fungal Esophageal Ulcer," *Clin. Nucl. Med.*, 6:332–333 (1981).

Reynolds, J. H., et al., "Imaging Inflammation with $^{99}Tc^{m}$ HMPAO Labelled Leucocytes," *Clin. Radiol.* 42:195–198 (1990).

Richter, J., "Heartburn, Dysphagia, Odynophagia, and Other Esophageal Symptoms," *Section III Esophagus*, Chapter 17, 331–340 (1993).

Rubin, R. H., "Editorial: In Search of the Hot Appendix–A Clinician's View of Inflammation Imaging," *J. of Nucl. Med.* 31:316–318 (Mar. 1990).

Rundback, J. H., et al., "Gallium-67 Imaging in Candidal Esophagitis," *Clin. Nucl. Med.*, 15:38–39 (May 22, 1989).

Sailer, J. F., and Janeway, C. M., "Pertechnetate Demonstration of a Barrett's Esophagus Involving the Length of the Esophagus," *J. of Nucl. Med.* 19:1366–1368.

Spiro, H. M., *Clinical Gastroenterology*, Fourth Ed., McGraw-Hill, Inc., 15–17 (1993).

Strauss H. W., et al., "Thallium-201: Non-Invasive Determination of the Regional Distribution of Cardiac Output," *Diag. Nucl. Med.* 18:1167–1170 (Aug. 4, 1977).

Tumeh, S. S., and Kaplan, W. D., "Thymic Uptake of Gallium-67 Citrate: Adult Versus Pediatric Patients," *J. of Nucl. Med.* 31:1746–1747 (Oct. 1990).

Weich, H. F., et al., "The Extraction of Thallium-201 by the Myocardium," *Circulation* 56:188–191 (Aug. 1977).

Weinstein, W. M., "Gastritis and Gastropathies," *Section IV Stomach and Duodenum*, Chapter 28, 545–571 (1993).

Wilton, G. P., et al., "Detection of Gastritis by $^{99m}Tc$-Labeled Red-Blood-Cell Scintigraphy," *AJR* 143:759–760 (Oct. 1984).

Yegelwel, E. J., et al., "Technetium Pertechnetate Esophageal Imaging for Detection of Barrett's Esophagus," *Digestive Diseases and Sciences* 34:1075–1078 (Jul. 1989).

Yeh, E., et al., "Gastric Gallium-67 Uptake in Gastritis," *Clin. Nucl. Med.* 8:605–607 (Dec. 1983).

NON-INVASIVE METHOD OF DETERMINING INFLAMMATION OF THE GASTROINTESTINAL TRACT

BACKGROUND OF THE INVENTION

The present invention relates to methods of detecting inflammation in the gastrointestinal tract of an organism.

The gastrointestinal tract includes the esophagus, stomach, small intestine, large intestine, and rectum. There are currently no routinely employed noninvasive diagnostic tests to identify inflammation of the gastrointestinal tract due to a variety of causes (Richter, Spiro, Weinstein). Current medical practice dictates that inflammation of the gastrointestinal tract be diagnosed by invasive endoscopic examination and biopsy of the tissue. This procedure involves increased risk of anesthesia, as well as bleeding and perforation of the gastrointestinal tract. Aside from this increased risk of morbidity, endoscopy requires a skilled endoscopist to perform the procedure.

There are only a few isolated case report descriptions in the medical literature of non-invasive tests to diagnose gastrointestinal inflammation. These previous case reports have demonstrated the use of a non-blood flow tracer, Gallium-67, to detect abnormal accumulations of Gallium-67 in the esophagus in severe cases of fungal esophagitis (Miller, Rundback), post-operative gastritis (Eikman), and coarse gastric mucosa (Hardoff). However, these reports have not concerned less severe and more common causes of inflammation. Also, Gallium-67 is not a blood flow tracer. None of these previous reports describes the use of blood flow tracers such as thallium-201 being used to identify inflammation in a tissue. Furthermore, none of these reports reveal the use of an artery dilating agent in conjunction with a blood flow tracer such as thallium- 201 for the non-invasive diagnosis of gastrointestinal inflammation.

Dipyridamole is a potent dilator of arteries. It is thought to act by stimulating the release of endogenous adenosine, which is known to stimulate gastric blood flow (Cho). None of the references cited at the end of this specification show use of dipyridamole to evaluate blood flow to the gastrointestinal tract, or to evaluate patients with gastrointestinal inflammation.

SUMMARY OF THE INVENTION

An object of the present invention is, therefore, to provide a reliable, sensitive and specific method of determining the presence or absence of inflammation in the gastrointestinal tract of an organism.

Yet another object is to provide such a method which is non-invasive, and has a lower rate of morbidity and complications than endoscopy.

Yet another object of the invention is to provide a relatively inexpensive and benign screening and diagnostic test for esophagitis and gastritis, which are exceedingly common but eminently treatable conditions.

Another object is to provide a method that will aid in readily distinguishing cardiac from gastrointestinal origins of pain.

Finally, it is an object of the invention to screen for and diagnose gastritis and esophagitis, which can often be treated with antibiotics and histamine antagonists. Other medical conditions, such as gastric adenocarcinoma and lymphoma or esophageal adenocarcinoma, also are associated with stomach inflammation and may also be diagnosed by this method. These latter conditions are potentially fatal if left untreated.

The present invention is a method of determining the presence of inflammation in the gastrointestinal tract of an organism, such as an animal (including humans). The method comprises the steps of introducing a blood vessel dilating agent (such as dipyridamole or adenosine) to dilate the arteries supplying blood flow to the gastrointestinal tract, introducing a blood flow marking medium into the circulatory system that supplies blood to the gastrointestinal tract, and determining the amount of marking medium appearing in the gastrointestinal tract.

In a preferred embodiment of the invention, dipyridamole is intravenously introduced into the circulatory system of a patient. Thallium-201 serves as the blood flow marking medium, which is injected into the circulatory system. The amount of thallium-201 extracted from the circulatory system by the gastrointestinal tract is measured as a function of time by a gamma camera to provide an indication of the amount of blood flow and inflammation in regions of the gastrointestinal tract. The inventor's present theory is that the amount of thallium-201 that is extracted by regions of the gastrointestinal tract is an indication of the severity of the inflammation that is present in that region because the thallium-201 may be taken up by the cells of the gastrointestinal tract itself or may be taken up into the excess edema fluid that usually accompanies the swelling of inflamed tissues. In either case a high blood flow to the region of inflammation induced by an arterial dilating agent such as dipyridamole will ensure that sufficient thallium-201 will be delivered to the region to allow enhanced extraction of the thallium-201 by the inflamed region.

Additional objects and advantages of the present invention will be apparent from the following detailed description of a preferred embodiment thereof, which proceeds with reference to the accompanying figures.

DETAILED DESCRIPTION OF THE PREFERRED EMBODIMENT

The present invention is a method of determining the presence of inflammation in a region of the gastrointestinal tract of an organism. Inflammation is a biological response to mucosal or mural injury, and includes such biological responses as reactive hyperemia and infiltration of inflammatory cells such as polymorphonuclear leukocytes and lymphocytes. Inflammation will be seen in conditions such as esophagitis, gastritis, gastric ulcer, duodenitis, duodenal ulcer, enteritis, ulcerative colitis, Crohn's disease, proctitis, and other conditions known to one skilled in this field.

The method is performed by introducing an artery dilating medication into the circulatory system that supplies blood flow to a region of the gastrointestinal tract being studied. Then a blood flow marking medium is introduced into the circulatory system that supplies blood flow to the same region. If the entire gastrointestinal tract is to be imaged, or if specificity of distribution to particular organs is not desired, intravenous administration can be employed. For example, these substances can be injected into an antecubital vein in the conventional manner. These substances will be distributed widely throughout the gastrointestinal tract by the systemic circulation, and will affect the entire gastrointestinal tract, including the blood supply of the region being studied.

Alternatively, these substances can be anatomically selectively introduced into arteries that supply specific anatomic regions of the tract. For example, a cannula can be introduced into the gastric artery to introduce the artery dilating medication and blood flow marking medium directly into the blood supply to the stomach. In this situation, the stomach or other specific region can be primarily visualized. It is anticipated, however, that in the preferred embodiment general systemic intravenous administration will be used to supply the dilating medication and blood flow marker to the region of the gastrointestinal tract being studied.

Figure 1:
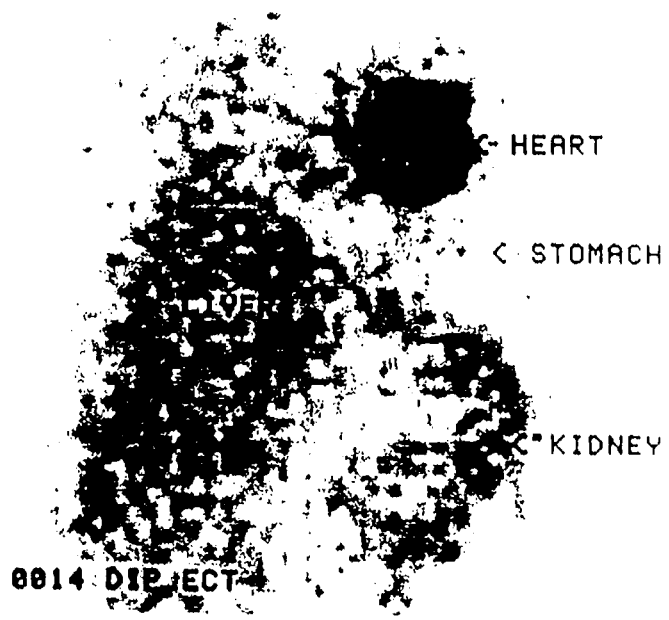
FIG. 1 is an image produced by scintillation photography with a gamma camera, showing the distribution of thallium-201 which had been introduced intravenously after a prior intravenous introduction of dipyridamole into the circulatory system. Although the heart and liver are well seen, there is no appreciable uptake of thallium-201 by the stomach in this 74 year old man who had no symptoms of stomach inflammation and who was not taking any stomach anti-inflammation medications.
Figure 2:
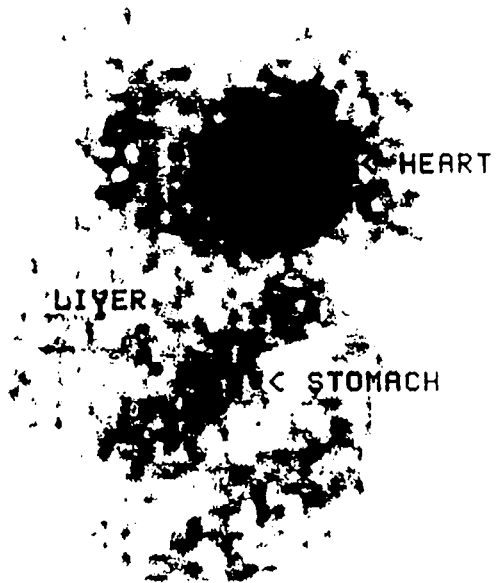
FIG. 2 is an image a 35 year old man with active symptoms of stomach inflammation and who was trying to control these symptoms with antacids. At the time of the images he had not taken the antacids for at least 12 hours. This post-dipyridamole image shows marked uptake of thallium-201 by the stomach such that the stomach uptake is more intense than the uptake by the liver. The liver is constantly visualized on post-dipyridamole thallium-201 images, hence it can be used as an internal standard against which one can compare intensity of thallium-201 uptake in the stomach or other regions of the gastrointestinal tract.

The amount of blood flow marking medium to appear in the region is then monitored, which provides an indication of the presence or absence of inflammation in that region of the gastrointestinal tract. Monitoring refers to observing the quantity of the medium concentrated in the tissue of interest, for example the stomach or esophagus in cases of suspected gastritis or esophagitis. The preferred embodiments will use a gamma camera to perform scintillation photography, which will produce a photographic image that correlates intensity of tissue uptake with darkness of the image. Hence in FIG. 1, blood flow is great in the heart, liver, and kidney, which have corresponding dark images on the photograph. The stomach does not have significant uptake, and has a correspondingly light image. However in FIG. 2, which shows a patient with gastritis, blood flow to the inflamed stomach is greater, and this increased uptake is seen as a darker image on the photograph.

In a particularly preferred embodiment of the method, dipyridamole is the arterial dilating agent that allows the increase in delivery of a blood flow marking medium or tracer such as thallium-201 to a region of the gastrointestinal tract which is inflamed by some disease process. These disease processes include but are not limited to gastritis, ulcers, esophagitis, enteritis, and colitis from a number of pathologic conditions including, but not limited to peptic ulcer disease, hiatus hernias, Helicobacter pylori infection, regional enteritis (Crohn's disease), ulcerative colitis, and diverticulitis. This increased uptake of the blood flow tracer can then be imaged using a gamma camera, and the identification of the increased tracer uptake can be used clinically to diagnose the presence of gastrointestinal tract inflammation.

The salutary effect of dipyridamole in determining the existence of inflamed tissue in the gastrointestinal tract was confirmed in a prospective study. The study population consisted of 39 consecutive patients experiencing chest pain syndromes who underwent a routine dipyridamole thallium-201 pharmacologic stress test. Patients were fasting from the night before the test and did not take their morning medications. The test was performed according to a standard protocol (Gould, Leppo). A dose of 0.56 mg/kg of dipyridamole was infused intravenously (for example into an antecubital vein) over four minutes to the supine patient. Serial blood pressures and 12 lead electrocardiograms were monitored. One to two minutes after cessation of the dipyridamole infusion, 3 mCi of thallium-201 was injected intravenously. Image acquisition was begun three to five minutes after the thallium-201 injection.

Using a large field of view gamma camera with a low energy, all purpose collimator, an anterior planar image was first obtained over five minutes. Next, a 180 degree tomographic imaging set was obtained consisting of 32 images, each of 30 seconds duration, starting at 45 degrees right anterior oblique and proceeding in 6 degree increments around the patient, ending at 45 degrees left posterior oblique. Delayed imaging was performed four hours after a second intravenous injection of thallium-201 (1 mCi). Both sets of raw image data underwent tomographic reconstruction for routine cardiac readings. However, for the purpose of assessing gastroesophageal thallium-201 uptake, both the initial 32 post-dipyridamole raw images as well as the four hour delayed images were displayed on a computer screen as cine loops. Without knowledge of the clinical history of the patient, these cine images were then interpreted by an experienced observer. The intensity of the thallium-201 uptake by the stomach and esophagus was graded in a semi-quantitative manner, using the liver as a consistently visualized internal standard, such that:

0=no uptake
1=mild uptake (<liver)
2=moderate uptake (=liver)
3=marked uptake (>liver)

Patients' symptoms and histories were obtained and recorded prospectively prior to the dipyridamole thallium-201 test from a direct interview with the patients and review of their medical record. Specifically, patients were questioned as to the presence or absence of current active symptoms of heartburn, dysphagia, epigastric discomfort related to meals and position, nausea, vomiting, or acid reflux (Richter, Spiro, Weinstein). Patients were also questioned as to the medications which they were taking, including prescription as well as over-the-counter medications. Past medical history concerning gastroesophageal diagnosis (hiatus hernia, peptic ulcer disease, etc.) and procedures (e.g., gastric surgery) were also obtained from the patients and their medical records (Table 1).

TABLE 1

CHARACTERISTICS OF THE PATIENT POPULATION
n = 39

| Category | n |
|---|---|
| Age (years) | 68 ± 2 |
| Sex (M/F) | 14/25 |
| NSAID | 3 |
| ASA | 8 |
| Prednisone | 5 |
| B-Blocker | 13 |
| Ca antagonist | 18 |
| Nitrate | 5 |
| Digoxin | 6 |
| Diuretic | 8 |

TABLE 1-continued

CHARACTERISTICS OF THE PATIENT POPULATION
n = 39

| Category | n |
| --- | --- |
| ACE inhibitor | |
| Anti-gastritis medications | 20 |
| Antacid | 5 |
| H2-blocker | 14 |
| Sucralfate | 0 |
| Omeprazole | 3 |
| Misoprostol | 1 |
| Hx HH | 10 |
| Hx PUD | 20 |
| Hx gastric surgery | 5 |
| NSAID | = non-steroidal anti-inflammatory medications |
| ASA | = aspirin |
| B-blocker | = beta adrenergic blockade |
| Ca antagonist | = calcium channel antagonist |
| ACE inhibitor | = angiotensin converting enzyme inhibitor |
| Anti-gastritis meds | = antacid, H2-blocker, omeprazole, sucralfate, misoprostol |
| H2-blocker | = ranitidine, cimetidine, pepcid |
| Hx | = history of |
| HH | = hiatus hernia |
| PUD | = peptic ulcer disease |

Statistical Analysis: Differences between groups were assessed by an unpaired t-test. To determine which variables had independent predictive value for gastric thallium-201 uptake by multivariate logistic regression analysis, the grading of the gastric uptake was dichotomized such that grades 0 and 1 were considered "no significant thallium-201 uptake," and grades 2 and 3 were considered "significant thallium-201 uptake." A p value of <0.05 was considered statistically significant. All data are expressed as mean±standard error of the mean.

In this study, 17 patients had active symptoms referable to gastritis, while 22 did not. Using the four point scoring system, patients with active symptoms of gastroesophageal discomfort were found to have a thallium-201 stomach uptake score on the initial post-dipyridamole images of 1.76±0.24. Conversely, patients without active symptoms had a score of 0.64±0.18, p=0.0001. In addition, patients previously identified by their physicians as requiring one or more anti-gastritis/anti-ulcer medications (n=20), showed significantly higher thallium-201 stomach uptake scores on their initial post-dipyridamole images, as compared to patients not receiving such medication (n=19), (1.55±0.27 vs. 0.68±0.15, respectively, p=0.009).

On the four hour delayed images, patients with and without active symptoms of gastric inflammation had thallium-201 scores of 1.53±0.27 and 0.45±0.16, respectively, p=0.0001. Patients who were and were not taking medications for symptoms of gastric inflammation had gastric thallium-201 scores of 1.25±0.27 and 0.58±0.18, respectively, p=0.05.

There were no significant differences in stomach thallium-201 uptake between patients on or off cardiac medications (i.e., beta blockers, calcium antagonists, nitrates, digoxin, diuretics, and angiotensin converting enzyme inhibitors). In addition, there were no statistically significant differences in gastric thallium-201 uptake in patients on or off other medications which have been associated with gastric irritation (e.g., prednisone, and non-steroidal anti-inflammatory drugs). However, the number of patients on these medications was low. Of the eight patients on aspirin, three were on low-dose enteric coated aspirin (325 mg/day) and none of the three had significant gastric thallium-201 uptake, whereas the one patient on high dose non-enteric coated aspirin (3000 mg/day) had 3+ uptake localized to the distal stomach. This patient had undergone upper endoscopy four months earlier, which had also shown inflammation in the distal part of the stomach.

To determine which factor or factors had independent predictive value of thallium-201 uptake on initial post-dipyridamole images, a stepwise logistic regression analysis was performed, using a dichotomous categorization of thallium-201 gastric uptake scores as either "significant" (2 or 3) or "not significant (0 or 1). Independent variables included in the analysis were active symptoms, anti-gastritis medications, age, a change in heart rate in response to dipyridamole, and a change in systolic blood pressure in response to dipyridamole. Only two of these variables had significant positive predictive value: the presence of active gastritis symptoms (p=0.0008) and the use the anti-gastritis medications (p=0.0008). Moreover, all of the patients with "significant" thallium-201 uptake (n=14) had active symptoms and/or were taking anti-gastritis medications.

Although dipyridamole is a potent dilator of arteries, other arterial dilators may be used in the alternative. These include adenosine and adenosine receptor agonists (e.g. cyclohexyladenosine, N-ethyl adenosine-5'-uroamide), nitroglycerine-type compounds (isosorbide dinitrate, isosorbide mononitrate), nitroprusside, forskolin hydralazine, and angiotensin converting enzyme inhibitors (e.g. lisinopril, captopril, enalapril, enalaprilat). Also, other blood flow marking mediums or tracers may be used as alternatives to thallium-201. These include but are not limited to technetium-99m labelled sestamibi (in a dose of 5-20 mCi) and teboroxime (5-20 mCi), rubidium-81 (1-5 mCi), rubidium-82 (15 mCi), potassium-43 (1-5 mCi), oxygen-15 labeled water (about 20 mCi), and copper-67 (5-15 mCi).

The artery dilating medication is introduced into the subject in a sufficient amount to dilate the arteries and increase the blood supply to the region of the gastrointestinal tract that is being scanned. For example, a dose of 0.56 mg/kg dipyridamole would be sufficient when administered intravenously to the subject. Doses of other arterial dilators that are known to produce generalized arterial dilation include 0.4 mg of nitroglycerin sublingually, 40 mg orally of isosorbide dinitrate, 20 mg of isosorbide mononitrate, and 60 to 120 mg orally of the calcium channel blocker diltiazem, or 30 to 60 mg orally of nifedipine. Adenosine is commercially available as Adenocard, which can be given in 6 or 12 mg doses. An example of an angiotensin converting enzyme inhibitor that can be used with the present invention is lisinopril, in a dose of 10-40 mg orally, or enalaprilat 1.25 mg IV.

The blood flow marking medium is a material, such as a radioactive tracer, that concentrates in areas of increased blood flow. It is infused in a dosage that is sufficient to show an increased uptake in areas of increased blood flow. In particular embodiments, it is an amount that is sufficient to show uptake equal to or greater than the liver uptake, in regions of the gastrointestinal tract (such as the stomach, esophagus or intestines) that are inflamed. For example, a dose of 3 mCi of thallium-201 would be sufficient to achieve this effect.

Gamma camera, or other flow tracer measurements, can begin as soon as the cardiovascular system has sufficient time to distribute the flow tracer to the gastrointestinal tract. Measurements may begin, for example, in 3 to 5 minutes after initial injection into the systemic vascular tree. Less time will be needed if injection is made directly into a branch artery supplying the region of interest, such as the gastric or superior celiac artery. Measurements can be made for several hours after injection, for example, 2–4 hours.

As used herein, a "region" of the gastrointestinal tract refers to a subdivision or subdivisions of interest. Such subdivisions include the esophagus, stomach, small intestine (and subdivisions thereof including the duodenum, jejunum, or ileum), large intestine (including subdivisions thereof, such as the ascending colon, transverse colon and descending colon), and the rectum. The liver is not considered a part of or a region of the gastrointestinal tract for purposes of this disclosure. The term "nitroglycerin or nitroglycerin-like compound" means nitroglycerin, nitroprusside, or other cognate drugs which are administered to humans in medical practice, and which dilate arteries.

Having illustrated and described the principles of the invention in a preferred embodiment, it should be apparent to those skilled in the art that the invention can be modified in arrangement and detail without departing from such principles. Therefore, the illustrated embodiment should be considered only as a preferred example of the invention and not as a limitation on the scope of the claims. I therefore claim as my invention all modifications and equivalents to the illustrated embodiment coming within the scope and spirit of following claims.

REFERENCES

1. Richter J. E. Heartburn, Dysphagia, Odynophagia, and Other Esophageal Symptoms. In: Sleisenger M. H. and Fordtran J. S., eds. Gastrointestinal Disease: Pathophysiology, Diagnosis, and Management. 5th edition. Philadelphia: W. B. Saunders Co.; 1993: 331.
2. Spiro H. M. Clinical Gastroenterology. 4th edition. New York: McGraw-Hill Inc., 1993: 15–17.
3. Weinstein W. M. Gastritis and Gastropathies. In: Sleisenger M. H. and Fordtran J. S., eds. Gastrointestinal Disease: Pathophysiology, Diagnosis, and Management. 5th edition. Philadelphia: W. B. Saunders Co.; 1993: 545–571.
4. Miller J. H., Thomas D. W. Uptake of gallium-67 in a fungal esophageal ulcer. Clin Nucl Med 1981; 6:332.
5. Rundback J. H., Goldfarb C. R., Ongseng F. Gallium-67 imaging in candidal esophagitis. Clin Nucl Med 1990; 15:38–39.
6. Eikman E. A., Tenocio L. E., Franlo B. A., Brady P. G., Williams J. W. Gallium accumulation in the stomach in patients with post-operative gastritis. J Nucl Med 1980; 21:706.
7. Hardoff R., Quitt M., Agahai E. Gastric visualization by gallium-67 scintigraphy and coarse gastric mucosa in a patient with Hodgkins disease in remission. Clin Nucl Med 1991; 16:124–126.
8. Gould K. L., Westcott R. J., Albro P. C., Hamilton G. W. Noninvasive assessment of coronary stenoses by myocardial imaging during pharmacologic coronary vasodilation: II. Clinical methodology and feasibility. Am J Cardiol 1978; 41:279–287.
9. Leppo J., Boucher C. A., Okada R. D., Newell J. B., Strauss H. W., Pohost G. M. Serial thallium-201 myocardial imaging after dipyridamole infusion: Diagnostic utility in detecting coronary stenoses and relationship to regional wall motion. Circulation 1982; 66:649–657.
10. Strauss H. W., Harrison K., Pitt B. Thallium-201: Non-invasive determination of the regional distribution of cardiac output. J Nucl Med 1977; 18:1167–1170.
11. Bonow R. O., Dilsizian V., Cuocolo A., Bacharach S. L. Identification of viable myocardium in patients with chronic coronary artery disease and left ventricular dysfunction: Comparison of thallium scintigraphy with reinjection and PET imaging with F-18-Fluorodeoxyglucose. Circulation 1991; 83:26–37.
12. Cho C. H., Ogle C. W. Modulatory action of adeonsine on gastric function and ethanol-induced mucosal damage. Dig Dis Sci 1990; 35:1334–1339.
13. Weich H. F., Strauss H. W., Pitt B. The extraction of thallium-201 by the myocardium. Circulation 1977; 56:188–191.

I claim:

1. A method of determining the presence of inflammation in a region of a gastrointestinal tract of a subject, comprising the steps of:

introducing an arterial dilating agent into the subject in a sufficient amount to dilate arteries to the region;

introducing a blood flow marking medium into the subject in a sufficient amount that the blood flow marking medium collects in an inflamed region of the gastrointestinal tract; and monitoring an amount of blood flow marking medium appearing in the region, thereby providing an indication of the presence or absence of inflammation in the region of the gastrointestinal tract.

2. The method of claim 1 in which the arterial dilating agent is selected from the group of arterial dilating agents consisting of dipyridamole, adenosine and other adenosine receptor agonists, nitroglycerin compounds, hydralazine, calcium channel antagonists, and angiotensin converting enzyme inhibitors.

3. The method of claim 1 in which the blood flow marking medium is selected from the group consisting of radiolabelled blood flow tracers selected from the group consisting of thallium-201, technetium- 99m labelled sestamibi and teboroxime, rubidium-81 and rubidium-82, potassium-43, oxygen-15 labelled water, and copper-67.

4. The method of claim 3 in which the monitoring step comprises quantitating an amount of blood flow marking medium present in the region of the gastrointestinal tract and liver of the subject by:

measuring the radioactive emissions produced by the blood flow marking medium in the region of the gastrointestinal tract and liver; and determining whether the measured emissions in the region of the gastrointestinal tract are less than, equal to, or greater than the measured emissions in the liver.

5. The method of claim 1 in which the region of the gastrointestinal tract is that of a human being.

6. A method of detecting esophagitis or gastritis in a subject, comprising the steps of:

injecting an intravenous dose of dipyridamole into a subject in a sufficient amount to dilate an arterial supply of the esophagus and stomach of the subject;

injecting an intravenous dose of thallium-201 into the subject in a sufficient amount to allow uptake of the thallium-201 into an inflamed esophageal or gastric mucosa;

monitoring emissions of gamma radiation with a gamma camera that images the esophagus, stomach and liver; and comparing an intensity of gamma emissions from the liver, esophagus and stomach to determine whether the gamma emissions of the esophagus or stomach are greater or less than gamma emissions from the liver.

7. The method of claim 6 wherein the dipyridamole is injected in a dose of at least 0.56 mg/kg, and the thallium-201 is injected intravenously in a dose of 3 mCi.

8. The method of claim 7 wherein the step of monitoring emissions comprises obtaining photographic images with the gamma camera, wherein areas of increased blood flow are darker than areas having less blood flow.

9. The method of claim 8 wherein the step of obtaining photographic images with the gamma camera comprises obtaining photographic images beginning 3 minutes after thallium-201 injection.

10. A method of detecting inflammation in a gastrointestinal tract of a human subject, comprising the steps of:

injecting an intravenous dose of at least 0.56 mg/kg of dipyridamole into the subject;

injecting an intravenous dose of 3.0 mCi thallium-201 into the subject;

beginning at least three minutes after injection of the thallium-201, monitoring emissions of gamma radiation with a gamma camera to provide images of the gastrointestinal tract and liver of the subject; and comparing an intensity of gamma emissions from the gastrointestinal tract to the liver to determine whether the gamma emissions from the gastrointestinal tract are greater or less than gamma emissions from the liver.

* * * * *